US00PP22412P2

(12) United States Plant Patent
Yates

(10) Patent No.: US PP22,412 P2
(45) Date of Patent: Dec. 27, 2011

(54) *BEGONIA* PLANT NAMED 'YASPED'

(50) Latin Name: *Begonia boliviensis*
Varietal Denomination: YASPED

(76) Inventor: Frederic C. Yates, Congleton (GB)

( * ) Notice: Subject to any disclaimer, the term of this patent is extended or adjusted under 35 U.S.C. 154(b) by 202 days.

(21) Appl. No.: 12/657,641

(22) Filed: Jan. 25, 2010

(51) Int. Cl.
*A01H 5/00* (2006.01)

(52) U.S. Cl. ..... Plt./343

(58) Field of Classification Search ..... Plt./343
See application file for complete search history.

(56) References Cited

U.S. PATENT DOCUMENTS

| | | | | |
|---|---|---|---|---|
| PP15,108 | P2 * | 8/2004 | Cross | Plt./343 |
| PP19,777 | P2 * | 2/2009 | Yates | Plt./343 |
| PP19,817 | P2 * | 3/2009 | Yates | Plt./343 |
| PP20,093 | P3 * | 6/2009 | Yates | Plt./343 |
| PP20,846 | P2 * | 3/2010 | Yates | Plt./343 |

OTHER PUBLICATIONS

UPOV ROM GTITM Computer Database, GTI Jouve Retrieval Software 2011/01 Citation for 'YASPED'.*

* cited by examiner

*Primary Examiner* — Wendy C Haas
(74) *Attorney, Agent, or Firm* — Penny J. Aguirre

(57) ABSTRACT

A new cultivar of *Begonia boliviensis* named 'YASPED', characterized by its dark red flowers, its compact, pendulant and full foliaged plant habit and its ease of propagation.

2 Drawing Sheets

Botanical classification: *Begonia boliviensis.*
Cultivar designation: 'YASPED'.

BACKGROUND OF THE INVENTION

The present invention relates to a new and distinct cultivar of *Begonia* plant, botanically known as *Begonia boliviensis* 'YASPED' and will be referred to hereafter by its cultivar name, 'YASPED'.

The new cultivar was derived from a controlled breeding program conducted by the inventor at his nursery in Congleton, Cheshire, U.K. The overall purpose of the breeding program is to make selections of *Begonia* plants with compact plant habits suitable for container use combined with superior flower performance and productive stock plants for propagation. 'YASPED' was selected in the Inventor's greenhouse in 2007 as a single unique plant from amongst the seedlings derived from a cross made in 2006 between an unnamed proprietary plant of *Begonia boliviensis* as the female parent and 'YABOS' (U.S. Plant Pat. No. 20,093) as the male parent.

Asexual reproduction of the new cultivar was first accomplished by terminal stem cuttings in Congleton, Cheshire, U.K. in 2007 by the Inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'YASPED' as a new and distinct cultivar of *Begonia.*

1. 'YASPED' exhibits a compact, pendulous plant habit.
2. 'YASPED' exhibits an abundance of side shoots to produce a full foliaged plant.
3. 'YASPED' exhibits dark red flowers.

4. 'YASPED' produces productive stock plants for propagation.

In comparison to its parents plants; the male parent, 'YABOS', differs from 'YASPED' in having larger flowers that are lighter red in color with tepals that are less rounded and in having a plant habit that is less compact habit and full. The female parent, an unnamed proprietary seedling, differs from 'YASPED' in having a less compact habit and flowers that are less red in color. 'YASPED' can be compared to the cultivar 'Bonfire' (U.S. Plant Pat. No. 15,108). 'Bonfire' differs from 'YASPED' in having a more upright and less pendulous plant habit and flowers that are smaller and less red in color. 'YASPED' can also be compared to cultivars from the same breeding program, which are similar in plant habit. 'Yagance' (U.S. Plant Pat. No. 19,817) differs from 'YASPED' in having bicolor pink and white flowers and 'Yamance' (U.S. Plant Pat. No. 19,777) differs from 'YASPED' in having flowers that are pink in color.

BRIEF DESCRIPTION OF THE DRAWING

The accompanying colored photographs illustrate the overall appearance and distinct characteristics of the new *Begonia.* The photographs in FIG. 1 and FIG. 2 were taken of a plant of 'YASPED' approximately 6 months in age as grown in a one-gallon container in Watsonville, Calif. The Photographs in FIG. 3 was taken of 3 plants of 'YASPED' approximately 6 months in age as grown in a two-gallon container in Congleton, U.K.

The photograph in FIG. 1 provides a side view of 'YASPED' in bloom and illustrates its full foliage.

Figure 1:
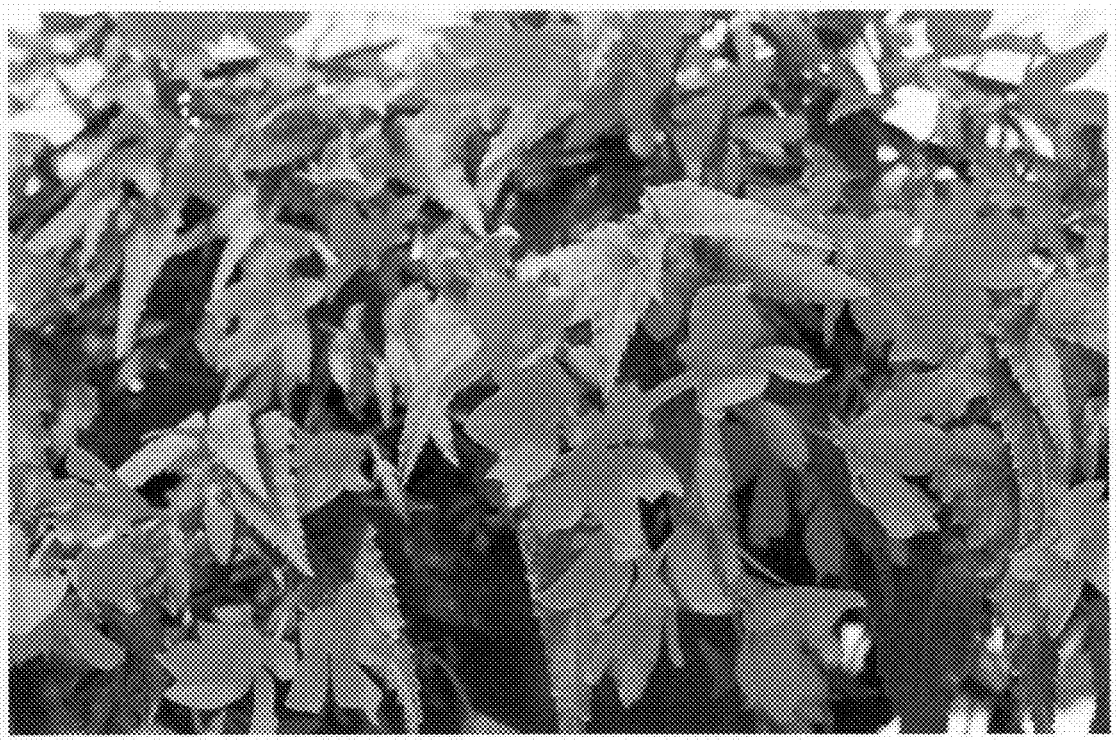
Figure 2:
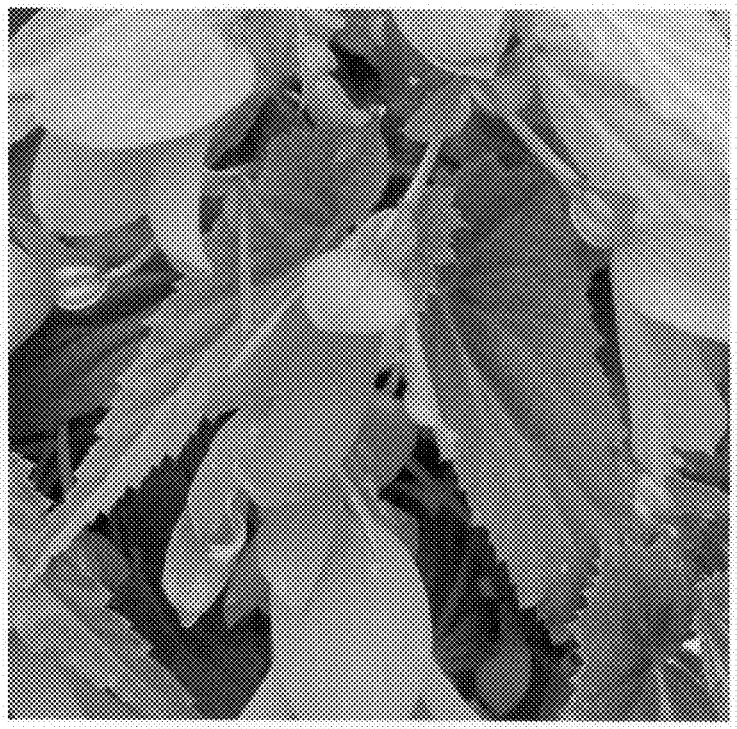

The photograph in FIG. 2 provides a close-up view of the flowers and foliage of 'YASPED'.

Figure 3:
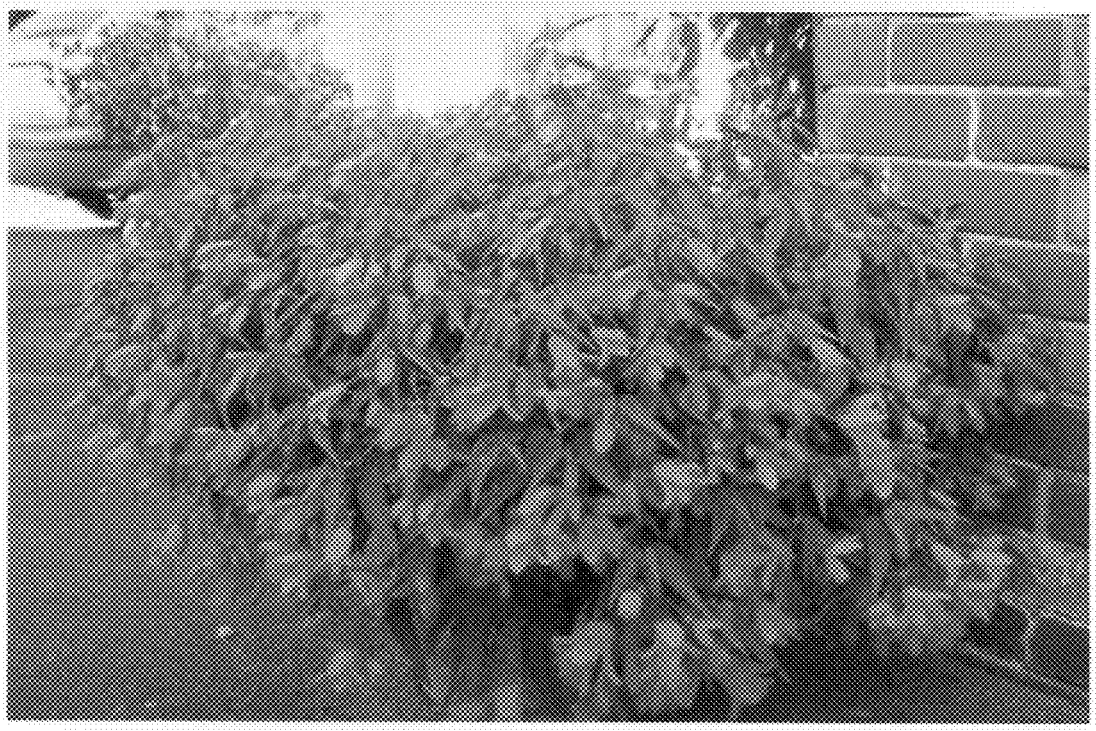

The Photographs in FIG. 3 provides a view of the plant habit of 'YASPED'.

The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately 3 months in age as grown in 4.5-inch containers under greenhouse conditions with ambient light in Congleton, Cheshire, U. K. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Botanical classification: 'YASPED' is a cultivar of *Begonia boliviensis*.

Parentage: Selection from unnamed proprietary selection of *Begonia boliviensis* as the female parent and 'YABOS' as the male parent.

General plant characteristics:

*Plant type.*—Deciduous tuberous perennial, grown primarily for use in baskets and containers.

*Plant habit.*—Compact, pendulous, full.

*Flowering period.*—From late March to November.

*Height and spread.*—Reaches about 40 cm in height and about 45 cm in spread.

*Cold hardiness.*—U.S.D.A. Zone 10.

*Culture.*—Grows in any commercial soil or growing media, 12 hours of light is needed for production in the winter months.

*Diseases and pests.*—No susceptibility or resistance to diseases or pests has been observed.

*Root description.*—Fleshy to fibrous with tubers produced for over-wintering.

*Tubers.*—Slightly flattened, irregularly lobed in shape and often depressed in center, an average of 4 cm in diameter (larger on older plants), surface is smooth and slightly corky, color 166C with corky patches 177B.

Growth and propagation:

*Growth rate.*—Typical vigor for the species but with more compact growth.

*Propagation.*—Terminal stem cuttings.

*Time required for root initiation.*—7 to 10 days at 20° C.

*Time required for root development.*—5 to 8 weeks to reach commercial size.

Stem description:

*Stem size.*—An average of 27 cm in length and 9 mm in width with lateral branches about 4 mm in width.

*Stem shape.*—Round, solid.

*Stem color.*—180B, becoming 181A.

*Stem surface.*—Smooth, glabrous, weakly glaucous, lenticels absent.

*Internode length.*—Average of 2.5 cm.

*Branching habit.*—Freely branched.

*Branching angle at emergence.*—About 70°.

Foliage description:

*Leaf shape.*—Asymmetric with one side narrowly ovate and the other side narrowly cordate and wider than the other.

*Leaf division.*—Simple.

*Leaf base.*—Weakly cordate.

*Leaf apex.*—Acuminate.

*Leaf venation.*—Pinnate, color 137D on upper surface and 144A on lower surface.

*Leaf margins.*—Irregular serrate with short bristles emerging from tips of the teeth.

*Leaf attachment.*—Petiolate.

*Leaf arrangement.*—Alternate.

*Leaf surface.*—Glabrous and smooth on upper and lower surface.

*Leaf color.*—Upper surface; 137C, lower surface; 147C tinged with 184D.

*Leaf size.*—Average of 15 cm in length and 3.4 cm in width.

*Leaf quantity.*—Average of 16 per branch.

*Leaf fragrance.*—None.

*Petioles.*—About 4.5 cm in length and 2 mm in width, surface is very sparsely pubescent with simple hairs, color is N170C.

*Stipules.*—Narrow-triangular in shape, 168C in color and rapidly becoming dry and papery, about 5 mm in length and 2 mm in width.

Flower description:

*Inflorescence type.*—2 to 3 flowered cyme produced sequentially in the axils of the upper leaves, monoecious with terminal male flowers developing before the lateral female flowers.

*Peduncles.*—About 4.3 cm in length and 2 mm in width, color; upper surface 180A, lower surface 179C, pubescence is absent.

*Flower persistence.*—Self-cleaning.

*Flower type.*—Single, rotate, un-fused tepals.

*Flower fragrance.*—None.

*Flower number.*—Average of 12 per inflorescence, one inflorescence per main stem.

*Flower aspect.*—Hanging.

*Bracts.*—2, present at base of cyme, broad ovate in shape, acute bifid apex, about 9 mm in length and 7 mm in width, color is 194C shading to 185C at margins.

Male flowers:

*Pedicels.*—About 2.1 cm in length and 1.5 mm in width, color; 34A on upper surface, 34C on lower surface, glabrous surface.

*Flower buds.*—Flattened ovoid in shape, about 2.5 cm in length and 1.9 cm in width, 47A in color.

*Flower size.*—About 4.1 cm in length and 6 cm in width.

*Tepals.*—4 in number (2 inner and 2 outer), outer tepals; ovate in shape, recurved near the apex, obtuse apex, rounded base, average of 4.2 cm in length and 2.1 cm in width, glabrous and smooth surface, entire margin, outer and inner tepals are a color between 50B and 43B on inner and outer surfaces.

*Corolla form.*—Spreading, tepals are un fused.

*Stamens.*—Numerous, connate below forming a tube, about 1.6 cm in length and 2 mm in width, 11A in color.

*Filaments.*—About 4 mm in length and 0.5 mm in width, 11A in color.

*Anthers.*—Broadly elliptic in shape, about 1 mm in length and <1 mm in width, 13A in color.

*Pollen.*—Abundant in quantity, 8C in color.

Female flowers:

*Pedicels.*—About 2.9 cm in length and 1.5 mm in width, color; upper surface 34A, lower surface 34C, glabrous surface.

*Flower buds.*—Flattened ovoid in shape, about 1.8 cm in length and 1 cm in width, 47A in color.

*Flower size.*—About 4.1 cm in length and 5.5 cm in width.

*Tepals.*—5 in number (3 inner and 2 outer), outer tepals; narrowly ovate in shape, acute apex, rounded base, average of 3.9 cm in length and 1.6 cm in width, glabrous and smooth surface, entire margin, inner tepals; narrow obelliptic in shape, recurved near the apex, acute apex, narrowly cuneate base, average of 4.1 cm in length and 1.3 cm in width, glabrous and smooth surface, entire margin, outer and inner tepals are a color between 50B and 43B on inner and outer surfaces.

*Corolla form.*—Spreading, tepals are un-fused.

*Styles.*—3 in number, cylindrical, connate for basal 1 mm, about 4 mm in length and <1 mm in width, 45C in color.

*Stigmas.*—Bifid in shape, lobes about 4 mm in length and <1mm in width, N26B in color.

*Ovaries.*—Inferior, about 9 mm in length and 8 mm in width (excluding wings), color is 144C, flushed 179B shading to 47A at tips of the wings.

*Seed.*—Numerous, ovoid in shape, 172C in color, <0.1 mm in size.

It is claimed:

1. A new and distinct cultivar of *Begonia* plant named 'YASPED' as herein illustrated and described.

* * * * *